United States Patent
Jeong (10) Patent No.: US 9,125,336 B2
(45) Date of Patent: Sep. 1, 2015

(54) METHOD OF INSPECTING BOARD

(75) Inventor: Joong-Ki Jeong, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 861 days.

(21) Appl. No.: 13/295,790

(22) Filed: Nov. 14, 2011

(65) Prior Publication Data

US 2012/0120414 A1 May 17, 2012

(30) Foreign Application Priority Data

Nov. 15, 2010 (KR) .......................... 10-2010-0113547

(51) Int. Cl.
| | |
|---|---|
| G01B 11/24 | (2006.01) |
| H05K 13/04 | (2006.01) |
| H05K 13/08 | (2006.01) |
| G01B 11/06 | (2006.01) |
| G01B 11/25 | (2006.01) |
| G01N 21/956 | (2006.01) |

(52) U.S. Cl.
CPC ............ H05K 13/08 (2013.01); G01B 11/0608 (2013.01); G01B 11/24 (2013.01); G01B 11/25 (2013.01); G01B 11/2513 (2013.01); G01B 11/2518 (2013.01); G01N 2021/95638 (2013.01); H05K 13/04 (2013.01); H05K 2203/15 (2013.01); H05K 2203/16 (2013.01); H05K 2203/168 (2013.01)

(58) Field of Classification Search
CPC ................. G06T 2207/30152; G01B 11/0608; G01B 11/25; H05K 13/04; H05K 2203/168; H05K 223/15; H05K 223/16
See application file for complete search history.

(56) References Cited

U.S. PATENT DOCUMENTS

| | | | | |
|---|---|---|---|---|
| 5,859,924 | A * | 1/1999 | Liu et al. ........................ | 382/145 |
| 6,490,368 | B2 * | 12/2002 | Roder ............................ | 382/147 |
| 7,641,099 | B2 * | 1/2010 | Nakagawa et al. ........... | 228/103 |
| 2002/0140949 | A1 | 10/2002 | Sasaki et al. | |
| 2010/0052664 | A1 | 3/2010 | Nishizawa et al. | |

FOREIGN PATENT DOCUMENTS

| | | |
|---|---|---|
| JP | 2002-296017 | 10/2002 |
| JP | 2009-008578 | 1/2009 |

\* cited by examiner

*Primary Examiner* — John Breene
*Assistant Examiner* — Christine Liao
(74) *Attorney, Agent, or Firm* — Kile Park Reed & Houtteman PLLC

(57) ABSTRACT

A method of establishing a tip location of a terminal includes establishing a virtual tip line by measuring a height of a board, on which a component having a terminal and a body is mounted, and comparing the measured measurement height with a predetermined reference height, establishing a central line with respect to a width direction of the terminal along a longitudinal direction of the terminal, and establishing a tip location of the terminal by using the measurement height along the central line from an intersection point of the virtual tip line and the central line. Thus, a tip location of a terminal may be more correctly acquired.

9 Claims, 6 Drawing Sheets

METHOD OF INSPECTING BOARD

CROSS REFERENCE TO RELATED APPLICATION

This application claims priority from and the benefit of Korean Patent Applications No. 2010-113547 filed on Nov. 15, 2010, which is hereby incorporated by reference for all purposes as if fully set forth herein.

BACKGROUND OF THE INVENTION

1. Field of the Invention

Exemplary embodiments of the present invention relate to a board inspection method for inspecting a component mounted on a board. More particularly, exemplary embodiments of the present invention relate to a board inspection method capable of inspecting a mounted state of a component by accurately detecting a terminal area of a component.

2. Discussion of the Background

Generally, at least one printed circuit board (PCB) is employed in an electronic device, and the PCB includes an element formed thereon such as a chip.

The element such as a chip is typically mounted on the PCB by using solder. In order to judge whether an element mounted on the PCB is good or bad or judge whether a pad, etc. connected to the element is good or bad, a terminal area and a solder area of the chip is required to be correctly established.

Conventionally, after capturing a two-dimensional image, the captured two-dimensional image has been used so as to determine goodness or badness of the element. However, it is difficult to discriminate the terminal area from the solder area in the two-dimensional image, because colors of the two-dimensional image are similar for each area and the two-dimensional image is sensitive to illumination, and area discrimination is not correct due to an effect incurred by noise of a camera.

Thus, an inspection method of a terminal capable of prevent the above described problems is required.

SUMMARY OF THE INVENTION

Exemplary embodiments of the present invention provide a method of establishing a tip location of a terminal capable of correctly discriminating a terminal area from a solder area by correctly acquiring a tip location of a terminal.

Additional features of the invention will be set forth in the description which is follows, and in part will be apparent from the description, or may be learned by practice of the invention.

An exemplary embodiment of the present invention discloses a method of establishing a tip location of a terminal. The method includes establishing a virtual tip line by measuring a height of a board, on which a component having a terminal and a body is mounted, and comparing the measured measurement height with a predetermined reference height, establishing a central line with respect to a width direction of the terminal along a longitudinal direction of the terminal, and establishing a tip location of the terminal by using the measurement height along the central line from an intersection point of the virtual tip line and the central line.

For example, the reference height may correspond to a tip thickness of the terminal, and the tip thickness of the terminal may be acquired from CAD information or component information of the board.

The virtual tip line may be established by extending a point based on a specific measurement height corresponding to a same height as the reference height, or based on a specific measurement height corresponding to a height selected from heights lower than the reference height by a user, in the width direction.

Establishing the central line may include establishing a first search section in the width direction of the terminal, acquiring a height profile with respect to the width direction of the terminal in the first search section, and establishing the central line with respect to the width direction of the terminal by using the height profile.

Establishing the central line may further include, after establishing the first is search section in the width direction of the terminal, establishing a second search section in the longitudinal direction of the terminal, and the height profile with respect to the width direction of the terminal may be acquired by being averaged for the second search section. The second search section may be established by regarding a position distant from the virtual tip line by a predetermined distance toward the body of the component as a start position so as to exclude an area in which solder is formed.

Establishing the central line with respect to the width direction of the terminal by using the height profile may include extracting a profile greater than or equal to a predetermined critical height from the height profile, and establishing the central line by extending a point having a maximum height in the extracted profile to be substantially parallel with the longitudinal direction of the terminal.

In an exemplary embodiment, establishing a tip location of the terminal by using the measurement height along the central line from an intersection point of the virtual tip line and the central line may include sequentially acquiring a change of the measurement height along the central line from the intersection point, and in case that the change of the measurement height exceeds a reference value, establishing the exceeded point as the tip location of the terminal.

In another exemplary embodiment, establishing the tip location of the terminal by using the measurement height along the central line from the intersection point of the virtual tip line and the central line may include establishing a change search section based on the intersection point, acquiring the change of the measurement height along the central line in the change search section, and establishing a point, at which the is change of the measurement height is maximum, as the tip location of the terminal.

According to the present invention, two steps, in which a tip line of a terminal of a component formed on a board is roughly established in advance and then is finely corrected, are performed, to thereby correctly establish a tip location of the terminal and also reduce calculation time required for establishing the tip location of the terminal.

In addition, an area of the terminal may be correctly established by correctly establishing the tip location of the terminal, to thereby correctly inspect whether the terminal is good or bad.

In addition, since the tip location of the terminal is established by using three-dimensional data based on height, the method of the present invention is little affected by color for each area and not sensitive to illumination, in comparison with defining a terminal area by using a two-dimensional image. Thus, the tip location of the terminal may be more correctly and easily established, and an effect incurred by noise of a camera may be reduced.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description is serve to explain the principles of the invention.

DETAILED DESCRIPTION OF THE ILLUSTRATED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
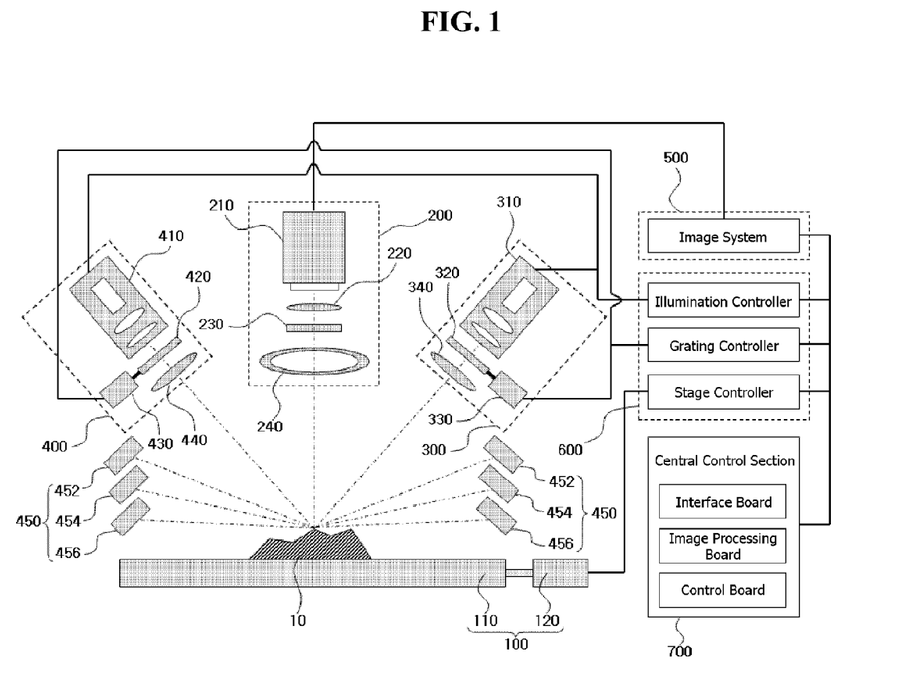
FIG. 1 is a schematic view illustrating a three-dimensional shape measurement apparatus used to a method of measuring a three-dimensional shape according to an exemplary embodiment of the present invention.

FIG. 1 is a schematic view illustrating a three-dimensional shape measurement apparatus used to a method of measuring a three-dimensional shape according to an exemplary embodiment of the present invention.

Referring to FIG. 1, a three-dimensional shape measurement apparatus used to a method of measuring a three-dimensional shape according to an exemplary is embodiment of the present invention may include a measurement stage section 100, an image capturing section 200, a first illumination unit including first and second projecting sections 300 and 400, a second illumination unit 450, an image acquiring section 500, a module control section 600 and a central control section 700.

The measurement stage section 100 may include a stage 110 supporting a measurement target 10 and a stage transfer unit 120 transferring the stage 110. In an exemplary embodiment, according as the measurement target 10 moves with respect to the image capturing section 200 and the first and second projecting sections 300 and 400 by the stage 110, a measurement location may be changed in the measurement target 10.

The image capturing section 200 is disposed over the stage 110 to receive light reflected by the measurement target 10 and measure an image of the measurement target 10. That is, the image capturing section 200 receives the light that exits the first and second projecting sections 300 and 400 and is reflected by the measurement target 10, and captures a plan image of the measurement target 10.

The image capturing section 200 may include a camera 210, an imaging lens 220, a filter 230 and a lamp 240. The camera 210 receives the light reflected by the measurement target 10 and captures the plan image of the measurement target 10. The camera 210 may include, for example, one of a CCD camera and a CMOS camera. The imaging lens 220 is disposed under the camera 210 to image the light reflected by the measurement target 10 on the camera 210. The filter 230 is disposed under the imaging lens 220 to filter the light reflected by the measurement target 10 and provide the filtered light to the imaging lens 220. The filter 230 may include, for example, one of a frequency filter, a color filter and a light intensity control filter. The lamp 240 may be disposed under the filter 230 in a circular shape to provide the light to the measurement target 10, so as to capture a particular image such as a two-dimensional shape of the measurement target 10.

The first projecting section 300 may be disposed, for example, at a right side of the image capturing section 200 to be inclined with respect to the stage 110 supporting the measurement target 10. The first projecting section 300 may include a first light source unit 310, a first grating unit 320, a first grating transfer unit 330 and a first condensing lens 340. The first light source unit 310 may include a light source and at least one lens to generate light, and the first grating unit 320 is disposed under the first light source unit 310 to change the light generated by the first light source unit 310 into a first grating pattern light having a grating pattern. The first grating transfer unit 330 is connected to the first grating unit 320 to transfer the first grating unit 320, and may include, for example, one of a piezoelectric transfer unit and a fine linear transfer unit. The first condensing lens 340 is disposed under the first grating unit 320 to condense the first grating pattern light exiting the first grating unit 320 on the measurement target 10.

For example, the second projecting section 400 may be disposed at a left side of the image capturing section 200 to be inclined with respect to the stage 110 supporting the measurement target 10. The second projecting section 400 may include a second light source unit 410, a second grating unit 420, a second grating transfer unit 430 and a is second condensing lens 440. The second projecting section 400 is substantially the same as the first projecting section 300 described above, and thus any further description will be omitted.

When the first grating transfer unit 330 sequentially moves the first grating unit 320 by N times and N first grating pattern lights are illuminated onto the measurement target 10 in the first projecting section 300, the image capturing section 200 may sequentially receive the N first grating pattern lights reflected by the measurement target 10 and capture N first pattern images. In addition, when the second grating transfer unit 430 sequentially moves the second grating unit 420 by N times and N second grating pattern lights are illuminated onto the measurement target 10 in the second projecting section 400, the image capturing section 200 may sequentially receive the N second grating pattern lights reflected by the measurement target 10 and capture N second pattern images. The 'N' is a natural number, and for example may be four.

In an exemplary embodiment, the first and second projecting sections 300 and 400 are described as an illumination apparatus generating the first and second grating pattern lights. Alternatively, the projecting section may be more than or equal to three. In other words, the grating pattern light may be illuminated onto the measurement target 10 in various directions, and various pattern images may be captured. For example, when three projecting sections are disposed in an equilateral triangle form with the image capturing section 200 being the center of the equilateral triangle form, three grating pattern lights may be illuminated onto the measurement target 10 in different is directions. For example, when four projecting sections are disposed in a square form with the image capturing section 200 being the center of the square form, four grating pattern lights may be illuminated onto the measurement target 10 in different directions. In addition, the first illumination unit may include eight projecting sections, and grating pattern lights may be illuminated onto the measurement target 10 in eight directions to capture an image.

The second illumination unit 450 illuminates light for acquiring a two-dimensional image of the measurement target 10 onto the measurement target 10. In an exemplary embodiment, the second illumination unit 450 may include a red illumination 452, a green illumination 454, and a blue illumination 456. For example, the red illumination 452, the green illumination 454, and the blue illumination 456 may be disposed in a circular shape over the measurement target 10 to illuminate a red light, a green light and a blue light, respectively, and may be disposed at different heights as shown in FIG. 1.

The image acquiring section 500 is electrically connected to the camera 210 of the image capturing section 200 to acquire the pattern images according to the first illumination unit from the camera 210 and store the acquired pattern images. In addition, the image acquiring section 500 acquires the two-dimensional images according to the second illumination unit from the camera 210 and stores the acquired two-dimensional images. For example, the image acquiring section 500 may include an image system that receives the N first pattern images and the N second pattern images captured in the camera 210 and stores the images.

The module control section 600 is electrically connected to the measurement stage section 100, the image capturing section 200, the first projecting section 300 and the second projecting section 400, to control the measurement stage section 100, the image capturing section 200, the first projecting section 300 and the second projecting section 400. The module control section 600 may include, for example, an illumination controller, a grating controller and a stage controller. The illumination controller controls the first and second light source units 310 and 410 to generate light, and the grating controller controls the first and second grating transfer units 330 and 430 to move the first and second grating units 320 and 420. The stage controller controls the stage transfer unit 120 to move the stage 110 in an up-and-down motion and a left-and-right motion.

The central control section 700 is electrically connected to the image acquiring section 500 and the module control section 600 to control the image acquiring section 500 and the module control section 600. Particularly, the central control section 700 receives the N first pattern images and the N second pattern images from the image system of the image acquiring section 500 to process the images, so that three-dimensional shape of the measurement target may be measured. In addition, the central control section 700 may control an illumination controller, a grating controller and a stage controller of the module control section 600. Thus, the central control section may include an image processing board, a control board and an interface board.

Hereinafter, a method of inspecting a terminal of a component mounted on a PCB, which is employed as the measurement target 10, by using the above described is three-dimensional shape measurement apparatus will be described in detail.

Figure 2:
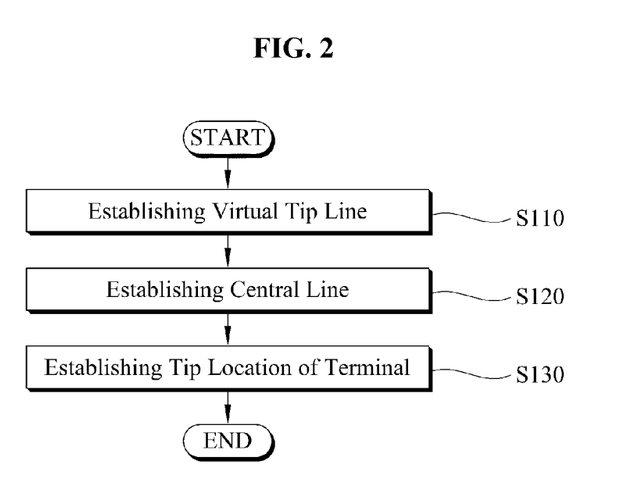
FIG. 2 is a flow chart illustrating a method of establishing a tip location of a terminal according to an exemplary embodiment of the present invention.
Figure 3:
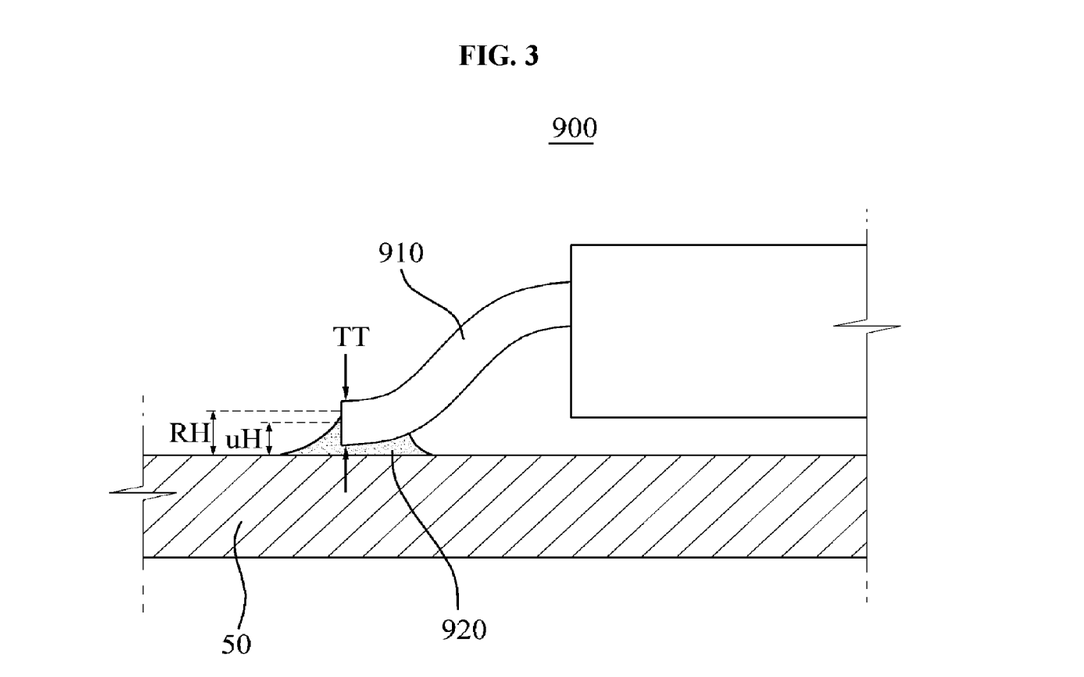
FIG. 3 is a cross-sectional view illustrating an example of a terminal and solder formed on a PCB.
Figure 4:
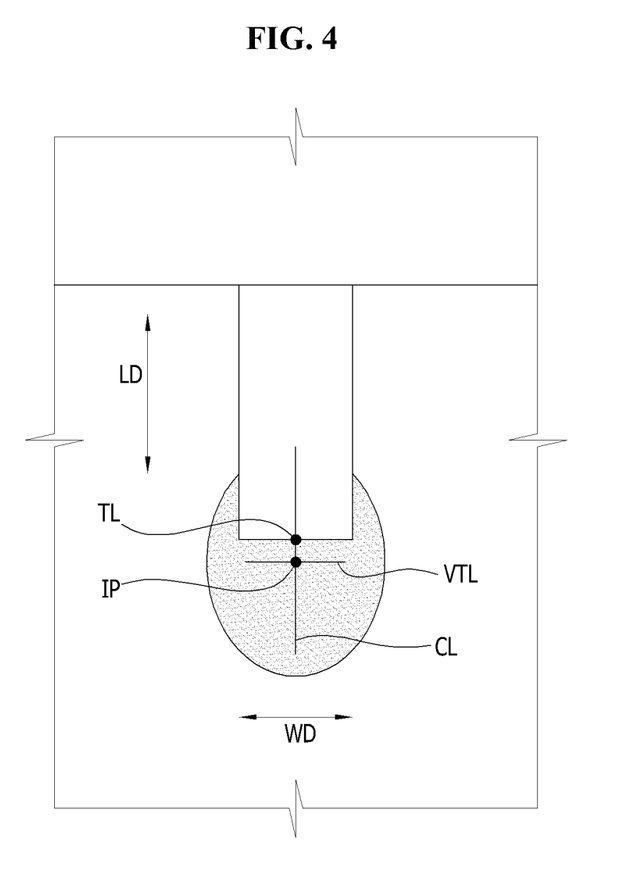
FIG. 4 is a plan view illustrating the method of establishing a tip location of a terminal in FIG. 2.

FIG. 2 is a flow chart illustrating a method of establishing a tip location of a terminal according to an exemplary embodiment of the present invention. FIG. 3 is a cross-sectional view illustrating an example of a terminal and solder formed on a PCB. FIG. 4 is a plan view illustrating the method of establishing a tip location of a terminal in FIG. 2.

Referring to FIGS. 2 to 4, in order to inspect a terminal according to an exemplary embodiment of the present invention, firstly, a virtual tip line VTL is established by measuring a height of a board 50, on which a component 900 having a terminal and a body is mounted, and comparing the measured measurement height with a predetermined reference height RH in step of S110. For example, the virtual tip line VTL is established by comparing the measurement height for a terminal 910 of the component 900 formed on the board 50 and solder 920 formed adjacent to the terminal 910 with the reference height RH.

In the present step, a tip location TL of the terminal 910 is roughly established, and the virtual tip line VTL corresponds to the rough tip location TL.

In an exemplary embodiment, the measurement height may be measured by using a measurement apparatus such as the three-dimensional shape measurement apparatus illustrated in FIG. 1.

The reference height RH corresponds to a height of a point at which a tip of the terminal 910 is expected to be located roughly, and for example, the reference height RH may be established to be substantially the same as a tip thickness TT of the is terminal 910. The tip thickness TT of the terminal 910 may be acquired from basic design information of the board 50, for example, CAD information or component information.

In an exemplary embodiment, comparing the measurement height with the reference height RH may be performed by comparing the measurement heights increasing from the left side to the right side in FIG. 3 with the reference height RH. In acquiring the measurement height, a cross-section is formed based on a line expected to be the center of the width direction WD of the terminal 910, and the measurement height may be acquired by measuring heights of the solder 920 for the cross-section. The line expected to be the center of the width direction WD of the terminal 910 may be acquired from basic design information of the board 50, for example, CAD information or component information.

The tip of the terminal 910 may be located at a little upper portion due to the solder 920 that may be located underneath the tip of the terminal 910. Thus, for example, in case that the reference height RH is established to be the same as the tip thickness TT of the terminal 910, a point at which the measurement height is the same as the reference height RH may be almost similar to a location at which the tip of the terminal 910 is located. Thus, the virtual tip line VTL may be established by extending a point based on a specific measurement height corresponding to a same height as the reference height RH in the width direction WD of the terminal 910.

Alternatively, the virtual tip line VTL may be established by extending a point based on a specific measurement height corresponding to a user height UH selected is from heights lower than the reference height RH by a user in the width direction WD of the terminal 910. For example, in case that the reference height RH is established to be the same as the tip thickness TT of the terminal 910, since the user height UH is selected from heights lower than the reference height RH, the measurement height may be searched with holding a spare height. Accordingly, in a step which will be described later, the location of the tip may be searched by regarding the user height UH selected from heights lower than the reference height RH as a start position, without an error in selecting a search section.

Then, a central line CL with respect to the width direction WD of the terminal 910 is established along a longitudinal direction LD of the terminal 910 in step of S120.

Hereinafter, an example of a method of establishing the central line CL is described in detail with reference to the accompanying drawings.

Figure 5:
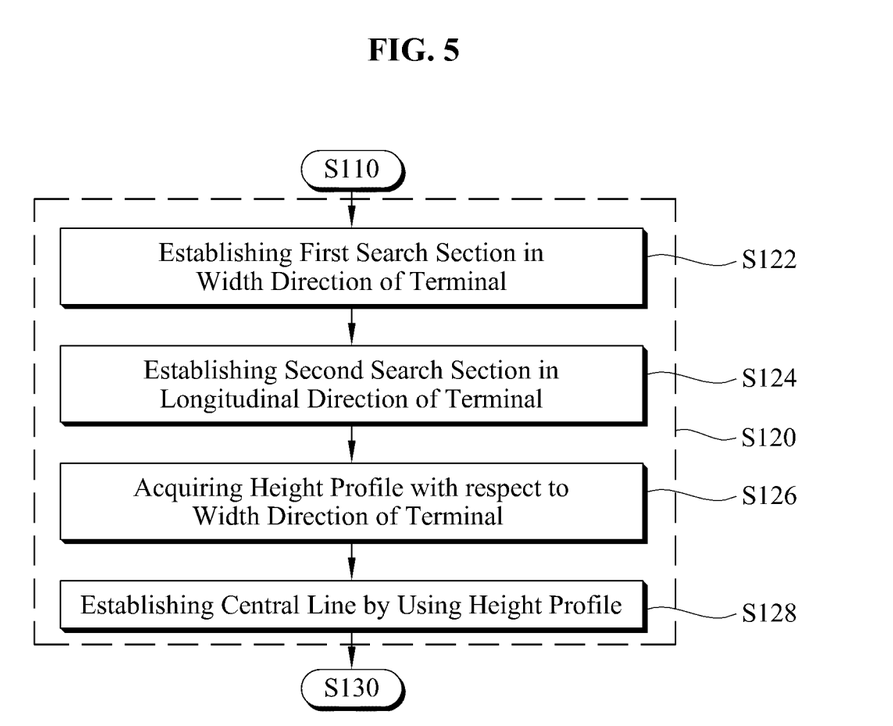
FIG. 5 is a flow chart illustrating a method of establishing a central line in FIG. 2.
Figure 6:
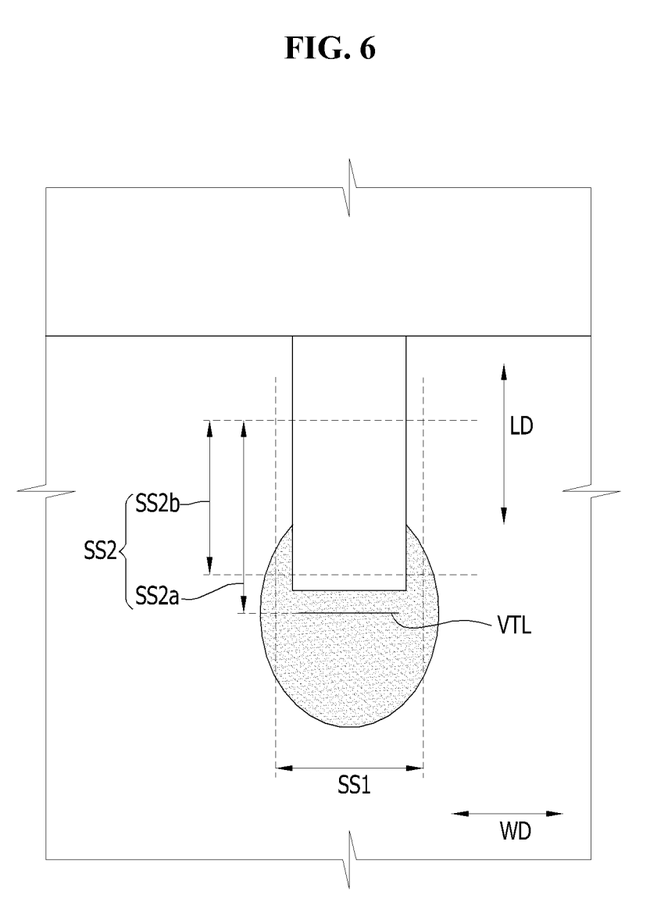
FIG. 6 is a plan view illustrating an example of a method of establishing the central line in FIG. 5.
Figure 7:
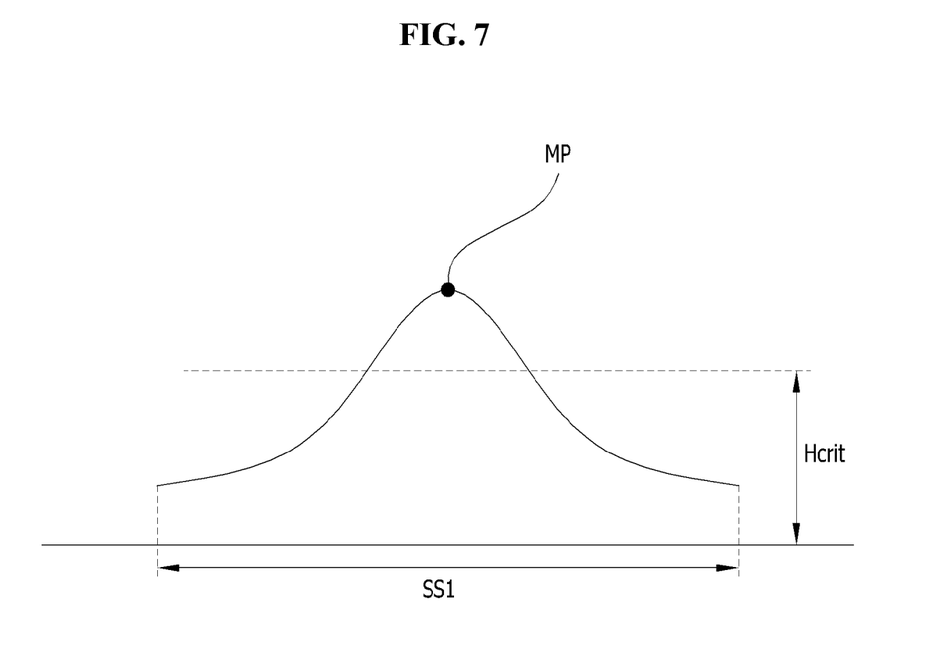
FIG. 7 is a graph illustrating an example of a height profile acquired in FIG. 6.

FIG. 5 is a flow chart illustrating a method of establishing a central line in FIG. 2. FIG. 6 is a plan view illustrating an example of a method of establishing the central line in FIG. 5. FIG. 7 is a graph illustrating an example of a height profile acquired in FIG. 6.

Referring to FIGS. 5 to 7, in order to establish the central line CL, firstly, a first search section SS1 is established in the width direction WD of the terminal 910 in step of S122.

Since the first search section SS1 corresponds to a section for establishing the central line CL, the first search section SS1 may be established to include all of the width of the terminal 910.

Then, a second search section SS2 is established in the longitudinal direction LD of the terminal 910 in step of S124.

The second search section SS2 may be established to include a predetermined area of the terminal 910 for securing data enough to establish the central line CL. In an exemplary embodiment, the second search section SS2 may be established by regarding the virtual tip line VTL as a start position, toward the body of the component, which corresponds to a reference numeral SS2a.

Thereafter, a height profile with respect to the width direction WD of the terminal 910 is acquired in the first search section SS1 in step of S126.

The height profile with respect to the width direction WD of the terminal 910 may be acquired by being averaged for the second search section SS2. A profile expressing height variations in the first search section SS1 may have a little different shape according to various positions of the second search section SS20. In addition, an error may occur in the profile expressing height variations due to noise. Thus, the height profile with respect to the width direction WD of the terminal 910 is acquired by being averaged for the second search section SS2, to thereby minimize an effect of noise in addition to considering all of the various positions of the second search section SS2. The height profile may be expressed, for example, in a curve form as shown in FIG. 7, and a point MP having the maximum height may be regarded as a point corresponding to the central line CL.

In case that the solder 920 is formed unsymmetrical, the height profile may be also formed unsymmetrical, and thus a portion at which the solder 920 is formed or a portion at which the solder 920 is expected to be formed may be excluded from the second search section SS2. For example, in step of establishing the second search section SS2 (S124), the second search section SS2 may be established by regarding a position distant from the virtual tip line VTL by a predetermined distance toward the body of the component as a start position, which corresponds to a reference numeral SS2b. Thus, an error of establishing the central line CL, which may incurred by unsymmetrical formation of the solder 920, may be prevented.

Then, the central line CL with respect to the width direction WD of the terminal 910 is established by using the height profile in step of S128.

In order to establish the central line CL with respect to the width direction WD of the terminal 910 by using the height profile, the central line CL may be established by extending the point MP having the maximum height to be substantially parallel with the longitudinal direction WD of the terminal 910.

In an exemplary embodiment, in order to remove noise and enhance data processing speed, a critical height Hcrit is established in advance, and a profile that is greater than or equal to the critical height Hcrit is extracted from the height profile. Then, the central line CL may be established by extending the point MP having the maximum height in the extracted profile to be substantially parallel with the longitudinal direction WD of the terminal 910.

Instead of the central line CL, a division line, which is divided for the width direction WD of the terminal 910 by a predetermined ratio, may be used. In this case, a tip location acquired in a process described later may be enlarged in the width direction WD by the predetermined ratio to acquire a real tip line that will be described later. That is, the central line CL may be an example of the division line, and may correspond to a division line that divides the width direction WD of the terminal 910 by 1:1.

Referring again to FIGS. 2 to 4, thereafter, the tip location TL of the terminal 910 is established by using the measurement height along the central line CL from an intersection point IP of the virtual tip line VTL and the central line CL in step of S130.

In the present step, the tip location TL of the terminal 910 is finely established by regarding the intersection point IP of the virtual tip line VTL and the central line CL, which is established in the previous steps of S110 and S120, as a start position. That is, the measurement height is finely checked along the central line CL from the intersection point IP and a position having a sudden change thereof is found, to thereby acquire the tip location TL of the terminal 910.

In an exemplary embodiment, in order to finely establish the tip location TL of the terminal 910, firstly, a change of the measurement height is sequentially acquired along the central line CL from the intersection point IP. Thereafter, in case that the change of the measurement height exceeds a reference value, the exceeded point is established as the tip location TL of the terminal 910. The reference value may be established as a value enough to find a point at which change of height suddenly occurs. The change of the measurement height may be, for example, a change of height itself, a rate of change of height, a differential coefficient of height, etc.

In another exemplary embodiment, in order to finely establish the tip location TL of the terminal 910, firstly, a change search section is established based on the intersection point IP. The change search section may be selected to have a section is enough to certainly include the tip location TL of the terminal 910. Then, the change of the measurement height is acquired along the central line CL in the change search section. Thereafter, a point, at which the change of the measurement height is the maximum, is established as the tip location TL of the terminal 910. The change of the measurement height may be, for example, a change of height itself, a rate of change of height, a differential coefficient of height, etc.

After establishing the tip location TL of the terminal 910 as described above, the tip location TL may be enlarged in the width direction WD of the terminal 910, to acquire a real tip line. In this case, in case of using a division line, which is divided for the width direction WD of the terminal 910 by a predetermined ratio, instead of using the central line CL, so as to establish the tip location TL of the terminal 910, an enlargement proportion of the width direction WD for acquiring the real tip line corresponds to the predetermined ratio of the division.

After the tip location TL or the tip line of the terminal 910 is established as described above, an area of the terminal 910 may be correctly established based on the tip location TL or the tip line. Thus, it may be inspected whether a component is mounted good or bad for the established area of the terminal 910.

As described above, two steps, in which a tip line of a terminal of a component formed on a board is roughly established in advance and then is finely corrected, are performed, to thereby correctly establish a tip location of the terminal and also reduce calculation time required for establishing the tip location of the terminal.

In addition, an area of the terminal may be correctly established by correctly establishing the tip location of the terminal, to thereby correctly inspect whether the terminal is good or bad.

In addition, since the tip location of the terminal is established by using three-dimensional data based on height, the method of the present invention is little affected by color for each area and not sensitive to illumination, in comparison with defining a terminal area by using a two-dimensional image. Thus, the tip location of the terminal may be more correctly and easily established, and an effect incurred by noise of a camera may be reduced.

As described above, the board inspection apparatus includes a plurality of work stages, and performs a board inspection independently for each work stage, to thereby greatly reduce time required for inspecting a board. In addition, an optical module moving part for moving an optical module including projecting parts is disposed over the optical module, and an image capturing part receiving grating pattern light generated from the projecting part is disposed at a side portion of the projecting part, to secure a space, which become small due to installing the work stages.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of establishing a tip location of a terminal formed on a board, comprising:

establishing a virtual tip line by measuring a height of a board, having a component including a terminal and a body mounted thereon, and comparing the measured measurement height with a predetermined reference height, by a central control section, wherein the virtual tip line is established by extending a point based on a specific measurement height corresponding to a same height as the reference height, or based on a specific measurement height corresponding to a height selected from heights lower than the reference height by a user, in a width direction of the terminal;

establishing a division line along a longitudinal direction of the terminal, the division line dividing a width of the terminal by a predetermined ratio, by the central control section; and establishing a tip location of the terminal by using the measurement height along the division line from an intersection point of the virtual tip line and the division line, by the central control section, wherein establishing the tip location of the terminal by using the measurement height along the division line from the intersection point of the virtual tip line and the division line includes sequentially acquiring a change of the measurement height along the division line from the intersection point and in case that the change of the measurement height exceeds a reference value, establishing the exceeded pint as the tip location of the terminal.

2. The method of claim 1, wherein the reference height corresponds to a tip thickness of the terminal.

3. The method of claim 2, wherein the tip thickness of the terminal is acquired from CAD information or component information of the board.

4. The method of claim 1, wherein establishing the division line includes:
    establishing a first search section in the width direction of the terminal;
    acquiring a height profile with respect to the width direction of the terminal in the first search section; and
    establishing the division line with respect to the width direction of the terminal by using the height profile.

5. The method of claim 4, wherein establishing the division line further includes, after establishing the first search section in the width direction of the terminal, establishing a second search section in the longitudinal direction of the terminal, and
    the height profile with respect to the width direction of the terminal is acquired by being averaged for the second search section.

6. The method of claim 5, wherein the second search section is established by regarding a position distant from the virtual tip line by a predetermined distance toward a body of the component as a start position so as to exclude an area in which solder is formed.

7. The method of claim 4, wherein establishing the division line with respect to the width direction of the terminal by using the height profile includes:
    extracting a profile greater than or equal to a predetermined critical height from the height profile; and
    establishing the division line by extending a point having a maximum height in the extracted profile to be substantially parallel with the longitudinal direction of the terminal.

8. The method of claim 1, wherein establishing the tip location of the terminal by using the measurement height along the division line from the intersection point of the virtual tip line and the division line includes:
    establishing a change search section based on the intersection point;
    acquiring the change of the measurement height along the division line in the change search section; and
    establishing a point, at which the change of the measurement height is maximum, as the tip location of the terminal.

9. The method of claim 1, wherein the division line includes a central line dividing the width of the terminal by 1:1.

* * * * *